(12) United States Patent
Howard et al.

(10) Patent No.: US 6,218,436 B1
(45) Date of Patent: *Apr. 17, 2001

(54) PHARMACEUTICALLY ACTIVE CAROTENOIDS

(75) Inventors: Alan N Howard, Cambridge (GB); John T Landrum; Richard A Bone, both of Miami, FL (US)

(73) Assignee: The Howard Foundation, Cambridge (GB)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/774,052

(22) Filed: Dec. 23, 1996

Related U.S. Application Data

(63) Continuation-in-part of application No. PCT/GB96/01368, filed on Jun. 7, 1996, and a continuation-in-part of application No. 08/487,627, filed on Jun. 7, 1995, now abandoned, which is a continuation-in-part of application No. 08/266,768, filed on Jun. 28, 1994, now abandoned, which is a continuation-in-part of application No. 08/219,897, filed on Mar. 30, 1994, now abandoned.

(30) Foreign Application Priority Data

| Jun. 28, 1993 | (GB) | ................................... | 93-13266 |
| Feb. 28, 1996 | (GB) | ................................... | 96-04221 |
| Jun. 7, 1996 | (GB) | ................................... | 96-11967 |

(51) Int. Cl.$^7$ .............................................. A61K 31/045
(52) U.S. Cl. .................................... 514/725; 514/912
(58) Field of Search .................................... 514/725, 912

(56) References Cited

U.S. PATENT DOCUMENTS

| 4,048,203 | 9/1977 | Philip . |
| 5,290,605 | 3/1994 | Shapira . |
| 5,310,764 | 5/1994 | Baranowitz et al. . |
| 5,457,135 | 10/1995 | Baranowitz et al. . |
| 5,523,494 | 6/1996 | Torres-Cardona et al. . |

OTHER PUBLICATIONS

Mares–Perlman, et al., "Serum Antioxidants and Age–Related Mascular Degeneration in a Population–Based Case–Control Study", Archives of Ophthalmology, Dec. 1995, vol. 113, pp. 1518–1523.

Seddon, et al., "Dietary Carotenoids, Vitamin A, C and E, and Advanced Age–Related Macular Degeneration", JAMA, Nov. 9, 1994, vol. 272, No. 18, pp. 1413–1420.

Snodderly, Evidence for protection against age–related macular deg eneration by carotenoids and antioxidants vitamins [1–3]. Am.J.Clin.Nutr., Dec., 1995, vol. 62, No. 6(Supplement), pp. 1448S–1461S.

Schalch, W., "Carotenoids in the retina—A review of their possible role in preventing or limiting damage caused by light and oxygen", Free Radicals and Aging (1992), pp. 280–298.

"The Effect of a Dietary Lack of Xanthophyll on the Eye of the Monkey", Nutr. Rev., Nov., 1980, vol. 38, No. 11, pp. 384–386.

Seddon, et al., "Do antioxidants prevent or retard the onset of AMD?", J. Am. Osteopath. Assoc., Jan., 1995, vol. 95, No. 1, p. 26.

J.T. Landrum et al., "Macular Pigment Steromens In Individual Eyes A Comparison Between Normals and Those with Age–Related Macular", Investigative Ophthalmology & Visual Science, Mar. 15, 1995, vol. 36, No. 4, Abst. No. 4094–75, p. S892.

Rousseau, E.J. N., "Carotenoids and Other Dietary Antioxidants in Free Radical Research: Protection of Human Retina Homogenate Against Photochemical and Metal–Induced Lipid Autoxidation", Dissertation Abstracts Online, vol. 34/02, of Masters Abstracts p. 733 (1994).

"Fat emulsion for injection, comprising carotenoid—used for intravenous supply of nutrition after operation", Derwent WPI, WPI Acc No.: 94–221775/27.

Buccal compsn., for preventing tooth decay and periodonal disease–contains xanthophyll(s) and/or carotene(s) contg. alpha–carotene: Derwent WPI, WPI Acc No.: 94–115117/14.

"Alpha tocopherol bitamin=A acid ester contg. oil compsn.—contg. carotenoid(s), used as cosmetic to inhibit skin deterioration and as antiulcer agent", Derwent WPI, WPI Acc No: 93–239918/30.

"Singlet–oxygen–removing compsn. –contains e.g. alpha or beta carotene and antioxidant, used for controlling peroxidation of lipid on skin", Derwent WPI, WPI Acc No: 94–012180/02.

"Pharmaceutical compsn. contg. heron egg yolk—for restoring balance between iron and gold in the blood", Derwent World Pat., WPI Acc No.: 80–90343C/51.

"Water–miscible carotenoid emulsions—contg tris(hydroxymethyl) amino methane soaps as emulsifiers", Derwent World Pat., WPI Acc No.: 74–11689V/07.

Chemical Abstracts 1996:69194 (1995). Secodderly.*

Chemical Abstract 122:79918 (1994). Seddon et al.*

* cited by examiner

*Primary Examiner*—Zohreh Fay
(74) *Attorney, Agent, or Firm*—Pillsbury Madison & Sutro LLP

(57) ABSTRACT

The carotenoids lutein and zeaxanthin are disclosed for pharmaceutical use in the treatment of advanced macular degeneration. High dosages are deployed to produce the high serum carotenoid levels needed to cause take-up by the macula.

23 Claims, 11 Drawing Sheets

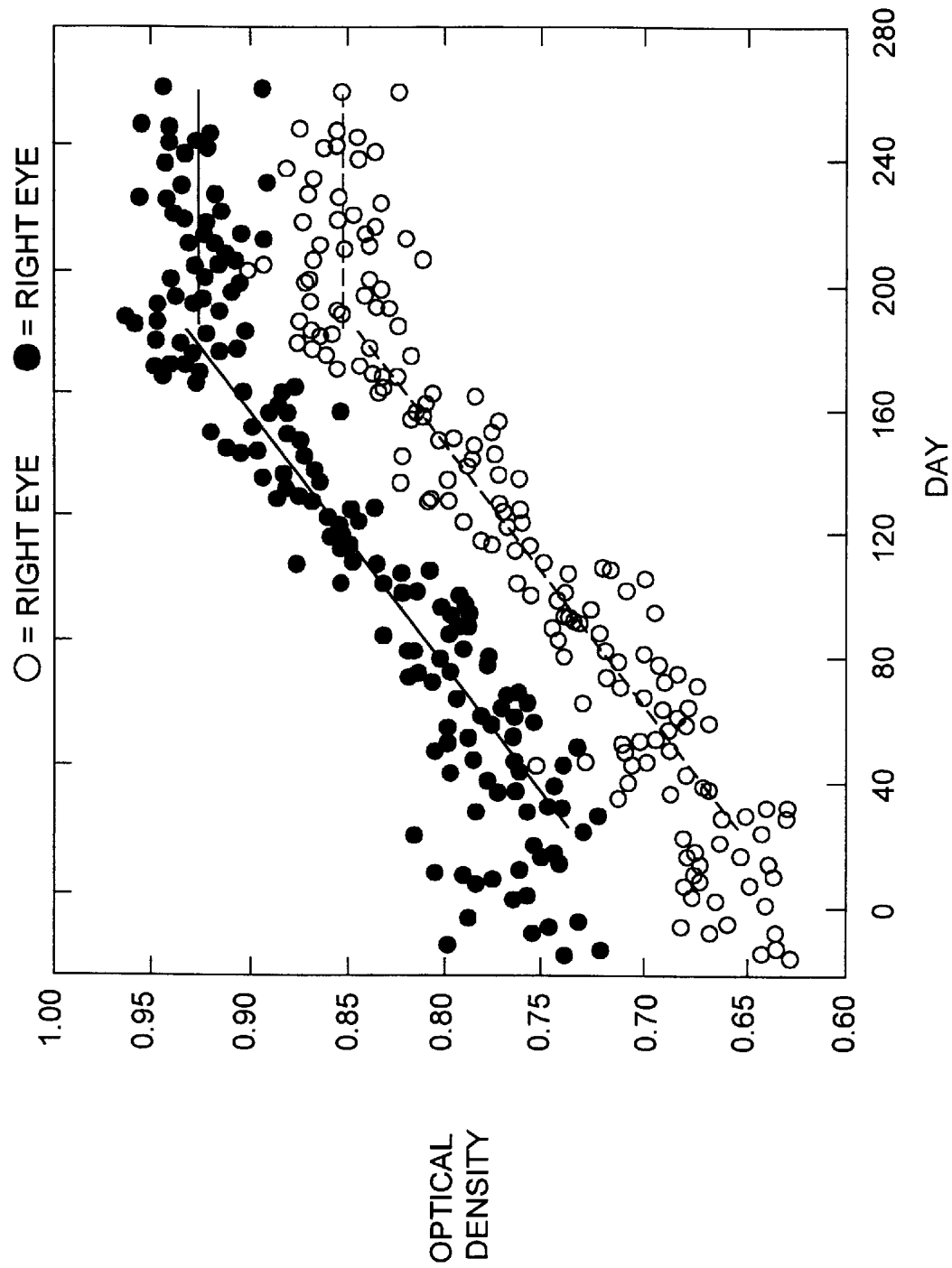

PHARMACEUTICALLY ACTIVE CAROTENOIDS

This application is a continuation-in-pat of PCT Application No. PCT/GB96/01368 filed Jun. 7, 1996 and of U.S. Ser. No. 08/487627 dated Jun. 7, 1995 now abandoned which is a continuation-in-part of U.S. Ser. No. 08/266768 dated Jun. 28, 1994 now abandoned which is a continuation-in-part of U.S. Ser. No. 08/219897 dated Mar. 30, 1994 now abandoned. The contents of all the foregoing applications are hereby incorporated by reference.

The invention related to the use of lutein and zeaxanthin which increase the deposition of macular pigment in the human eye. The invention is particularly but not exclusively concerned with lutein and/or zeaxanthin for use in the treatment by therapy or prophylaxis of disease of the macula and in particular age-related macular degeneration (AMD).

The macula is the anatomical region of the retina which in man is responsible for central vision. Centered on the fovea, where the visual axis meets the retina, it extends radially outwards to a distance of about 2.75 mm (Davson, 1990). The macula is divided into the inner macula and the outer macula. The inner macula extends radially out to a distance of 1.5 mm while the outer macula is defined by the surrounding annular ring. The central part of the macula is easily recognisable because of its yellow coloration which results from the presence of macular pigment.

Despite its small size the macula is endowed with the highest degree of visual acuity. It is therefore not surprising that considerable effort is devoted to understanding and, when possible, treating diseases which disrupt the normal functioning of the macula. One such disease is age-related macular degeneration (AMD) which occurs in about 20% of the population above the age of 65 and is the leading cause of visual impairment in the USA and UK. AMD has up to the present been an irreversible condition.

Pooled extracts of the macular pigment were found by Wald ((1945) to have a carotenoid-like absorption spectrum which appeared to match that of luetin. Further work in the 1980's demonstrated that it consisted of lutein and zeaxanthin (Bone et al 1985).

More recent work (Bone et al 1993) has shown that the zeaxanthin component found in the human retina is itself composed of all three of the possible stereoisomers. FIG. 1 shows the stereochemical structures of the macular pigment components. The 3' hydroxy groups on lutein and meso-zeaxanthin have the same absolute configuration making interconversion possible by a movement of the 4'–5' double bond (lutein) to the 5'–6' position (meso-zeaxanthin). Of the three stereoisomers, SSZ is present only as a relatively small component, RRZ is of dietary origin whereas RSZ (for meso-zeaxanthin) is not common in the diet and has yet to be detected in human serum. It has been suggested that the presence of RSZ may be the result of isomerization of lutein to RSZ by an enzyme.

The function of he macular pigment has not been unequivocally determined. It has been proposed that one function may be to reduce the adverse effect of chromatic aberration in the ocular media thereby increasing acuity (Walls 1967: Reading and Weale 1974). Currently, a more generally held view is that the pigment probably acts in a protective capacity against the damaging effects of blue light (Dicthburn 1973, Kirshfeld 1982, Bone et al 1984) which can induce the formation of reactive free radicals within the retina and the formation of such species may be greatly reduced in individuals having a high level of macular pigmentation. The macular pigment may also serve passively as a filter and shield sensitive tissues from harmful excessive blue light.

AMD is a disease which develops gradually over a period of many years with loss of sight being the ultimate result. The damaged tissue has an unusually high lipid content which it is has been suggested oxidises to form lipofuscin, a fluorescent product of lipid oxidation. It has been postulated that exposure of the retina to excessive blue light may increase the rate of lipofuscin formation. (Feeney-Burns et al 1990, Gottsch et al 1990).

To date, little is known about the factors which influence the uptake of carotenoids into the macula and there is no effective cure or prevention of AMD.

The studies of plasma carotenoids in case control studies of AMD have been equivocal. In the Beaver Dam eye study (Mares-Periman et al 1995), no differences were observed in 167 cases and 167 control in serum including lutein or zeaxanthin. In the Eye Disease Case Control Study Group (1993) results of 421 cases and 615 controls were reported. People with serum carotenoid levels in the medium to high group had one half to one third risk of AMD. All the carotenoids measured including lutein, zeaxanthin, beta carotene, alpha carotene and cryptoxanthin were implicated. In a further publication (Seddon et al, 1994), there authors found that the consumption of lutein and zeaxanthin (which are primarily obtained from dark green leafy vegetables) were most strongly associated with a reduced risk for AMD. However, some people with a high consumption of green vegetables still suffered from AMD.

In an abstract published in the March 1995 issue of Investigative Opthamology and Visual Science (36, suppl, 892), the carotenoid analysis of 8 normal eyes and 8 eyes from patients with AMD was reported. The results suggested a positive correlation existed between lowered macular pigment and the prevalence of AMD, but recommended that caution should be exercised in this interpretation because the reduced macular pigment could be a result, rather than a cause, of the disease. When the subject-matter of the above mentioned abstract was submitted for publication to a peer-reviewed journal, the referees recommended rejection because the number of samples analysed was too small. Further results were therefore necessary before any conclusion could be made on the possible preventative role of lutein/zeaxanthin in AMD.

It is the object of the present invention to increase macular pigment and to prevent or cure AMD by the administration of lutein and/or zeaxanthin.

It is a further object of the invention to provide a method of treatment of AMD by the use of lutein and/or zeaxanthin and further to provide a novel composition comprising these two hydroxy carotenoids in combination.

Within the above context we have now found surprisingly that by selecting a particular type of carotenoid namely lutein/zeaxanthin or an ester thereof it is possible to increase the macular pigment in the human macula which could lead to the prevention and/or treatment of AMD in those people at risk or with the disease.

Moreover the effective does is rather surprisingly greater than that which is normally achieved by the intake of lutein/zeaxanthin in rich green vegetables. While it could be suspected that since the macula contains lutein/zeaxanthin, the administration of lutein/zeaxanthin in quantities similar to that occurring in green vegetables would raise the concentration of macular pigment, it has been found rather surprisingly that when the caroteinoids are given orally in a concentrated form the amount required to be effective in the short term is considerably greater than expected.

Furthermore, it has ben found that in a sufficiently large enough sample to warrant conclusions, the lutein/zeaxanthin content of the retinas of eyes from people with AMD was 30% less than people with normal eyes.

Accordingly, the present invention in one aspect provides lutein/zeaxanthin or a mixture thereof for the use as a pharmaceutical or food supplement, particularly in the elevation of macular pigment and the prevention or management of age-related macular degeneration. For this purpose, the mixture can contain 10 to 90% of each carotenoid mixed with the other. Generally speaking, the active agent or agents (ie lutein and/or zeaxanthin) may be used in the total dosage regime of up to 100 mg per day typically 10–50 mg per day with an optimum dosage of 30 mg per day.

The dose depends on the time of administration. When the macula is depleted of macular pigment, a high dose (circa 30 mg/day) is normally used. Treatment methods according to the invention are principally directed to high dosage of the patient (ie amounts of 10 mg/day or higher) and are especially concerned in preferred embodiments to achieve serum levels of the carotenoid(s) of at least 0.7 or 0.8 mm/ml.

During the initial period of administration, it is preferred to use a large dose of circa 30 mg/day for several weeks. However, when a plateau is achieved in the concentration of macular pigment a maintenance dose of eg circa 7.5 mg/day is preferable. The reason for this is that at the high dose, the skin turns yellow caused by the yellow colour of lutein/zeaxanthin. This is an undesirable side-effect. Whilst it can be tolerated for a short time, a lower dose is preferable for maintenance since it is sufficient to maintain the level of macular pigment to a desirable level, and does not cause skin pigmentation.

A unit dosage form such as say a 750 mg tablet or say an 800 mg capsule to be used on a one-a-day basis may contain from 0.1% to about 12.5% by weight of lutein and other ingredients may comprise:

Beta carotene about 2 to about 20 mg e.g. about 5 mg
Lycopene about 2 to about 20 mg e.g. about 5 mg
Vitamin A about 400 to about 600 RE e.g. about 500 RE
Vitamin C about 75 to about 250 mg e.g. about 100 mg
Vitamin E about 50 to 250 mg e.g. about 100 mg
Solenium about 80 to about 120 mcg e.g. about 90 mcg
Copper about 2 to about 4 mg e.g. about 3 mg
Zinc about 10 to about 20 mg e.g. about 15 mg
Manganese about 2 to about 5 mg e.g. about 4 mg
Ubiquinone about 10 to about 100 mg e.g. about 50 mg (Coenzyme O10)
Carrier about 150 to about 250 mg e.g. about 175 or about 200 mg Accordingly the invention consists of high dose of lutein/zeaxanthin followed by a lower dose when the macular pigment reaches a plateau. For those skilled in the art, macular pigmentation can be measured by a flicker photometer (see Example 2).

In carrying out the invention, it is preferred to administer the di-hydroxy carotenoids lutein and/or zeaxanthin or an ester thereof. The compounds of the invention are especially useful in increasing the macular pigment in the human macula and in the preventive treatment of age-related macular degeneration.

As will be seen from FIG. 1 of the drawings, lutein and zeaxanthin are stereoisomers. Zeaxanthin can exist in three different forms in nature, namely zeaxanthin (the 3R, 3'R form) meso-zeaxanthin (the 3R, 3'S form) and 3S, 3'S zeaxanthin.

All forms can be utilised individually or a mixture thereof obtained from natural products or synthetically. However, lutein and mesozeaxanthin are preferred. Mesozeaxanthin is an isomer which does not occur naturally (at least in any abundance) other than in he primate eye, and is thought to be synthesized in the eye by enzymatic conversion.

In carrying out the invention, there may be used a compound as defined in its free form or in the form of an ester. Typically such esters are $C_1$ to $C_{18}$ esters e.g. ethyl esters, or esters with long chain fatty acids e.g. lauric myristic or palmitic esters or naturally occurring esters such as lutein ester from certain plants e.g. marigold.

In another aspect, the invention provides a food supplement or pharmaceutical composition, which composition comprises lutein/zeaxanthin or an ester thereof together with a food supplement or pharmaceutically accepted diluent or carrier.

Such a composition may be in bulk form, or more preferably, unit dosage form. Thus, for example, the composition may be formulated as a tablet, capsule, powder, solution or suspension.

Compositions in accordance with the invention may be prepared using the carotenoid or ester active agent in accordance with conventional food supplement or pharmaceutical practice. The diluents, excipients or carriers which may be used are well known in the formulation are and the form chosen for any particular regimen will depend on the given context and the formulator's choice.

Lutein/zeaxanthin can be provided as a vegetable food, the vegetable being the harvest of a plant containing the lutein/zeaxanthin. The plant may be native or, more preferably, may be a genetically-modified plant (GMP) in which the lutein/zeaxanthin synthesis capacity is enhanced.

Such GMPs (eg lutein-enriched tomatoes) are particularly useful because, during the initial phase of administration of lutein/zeaxanthin, there is insufficient active carotenoid present in ordinary vegetables to effect a significant increase in macular pigment in a short period. By raising the levels of lutein/zeaxanthin to levels several times normal (say 5–10 fold) a very effective product is achieved which can raise macular pigment levels in the same time as the administration of capsules containing 15–30 mg lutein/zeaxanthin.

Lutein can be increased in plants (for instance tomatoes) by manipulation and cloning of genes in the carotenoid synthesis (FIG. 6) according to the methods described in Bartley G E Scolnik, PA & Guiliano (1994) Ann Rev Plant Physiol Plant Mol Biol 45, 287–301 using either genes from plants or micro-organisms. Especially important are one or more of the trans genes which control the levels of or express the genes involved in the enzymes of the cartenoid synthetic pathway more specially: GGPP synthase, phytoene synthase, phytoene desaturase, lycopene cyclaso and alpha-carotene hydrolase.

The invention includes within its scope lutein/zeaxanthin for use as a pharmaceutical. It is thought that when administering lutein/zeasxanthin, in he above form, the patient will benefit through a synergism between the lutein/zeaxanthin and other substances in the plant.

Genetic modification of plants for the purposes of the invention may be effected by following the methods disclosed in PCT Application No. WO92/16635 and analogous methods.

In carrying out the invention, the active carotenoid(s) may be used together with other active agents. Amongst such other agents, there may be mentioned, for example, the following, namely another carotenoid such as lycopene or alpha, beta, gamma or delta carotene, or one or more of the following antioxidants, namely vitamin A, vitamin C, vitamin E (α-tocopherol and other active tocopharols), selenium, copper, zinc, manganese and ubiquinone (coenzyme Q10).

Use of a mixture containing a tocopherol such as α-tocopherol is especially preferred since it is believed that such a mixture affords a synergistic effect.

The carotenoids are partially destroyed in the gastrointestinal tract by oxidation. By adding vitamin E and/or vitamin C, this process in inhibited and more carotenoid is absorbed. The inhibitor may be included as part of a composition as part of the invention or administered separately.

In addition to the above aspects, the invention includes the use of the carotenoids, lutein/zeaxanthin or an ester thereof, for increasing the pigment in the macula of the human eye or treatment for prevention of age related macular degeneration or other macular pigment depreciation malady.

Furthermore, the invention includes a process for the manufacture of a food supplement or medicament for the above-mentioned purposes.

Still further, the invention includes a method for the increase of macular pigment in the human eye or for prevention of age-related macular degeneration comprising of administering an effective amount of lutein/zeaxanthin or mixture thereof.

BRIEF DESCRIPTION OF THE DRAWINGS

The following Examples are intended to illustrate the invention by way of example only. Reference in the Examples is made to FIGS. 2 to 4 of the drawings, wherein:

FIG. 4c shows daily macular pigment optical density measurements for the same subject as is the case in FIG. 4b for a longer period of lutein administration which includes the period represented in FIG. 4b.

EXAMPLE 1

1.1 Analysis of carotenoids in eyes

An HPLC analysis of retinas obtained for normal and AMD individuals was conducted using a sufficiently large sample to warrant conclusions on the importance of macular lutein and zeaxanthin in the prevention of AMD. The amount and distribution of the macular carotenoids, including the stereo isomers, were determined and compared for 15 normal and 22 AMD eyes in order to determine if there is evidence for or against the hypothesis that macular pigment protection from light exposure plays a significant role in reducing AMD.

For each normal and AMD eye, the neural retina was cut into a central disk and 2 concentric annuli using trephines of 3, 11 and 21 mm. To extract the carotenoids, the tissues were ground in ethanol/water (1:1) to which 10 ng lutein monomethyl ester was added as an internal standard. Separation and quantitation of zeaxanthin and lutein fractions was by reversed-phase HPLC using Phenomenex column.

Figure 1:
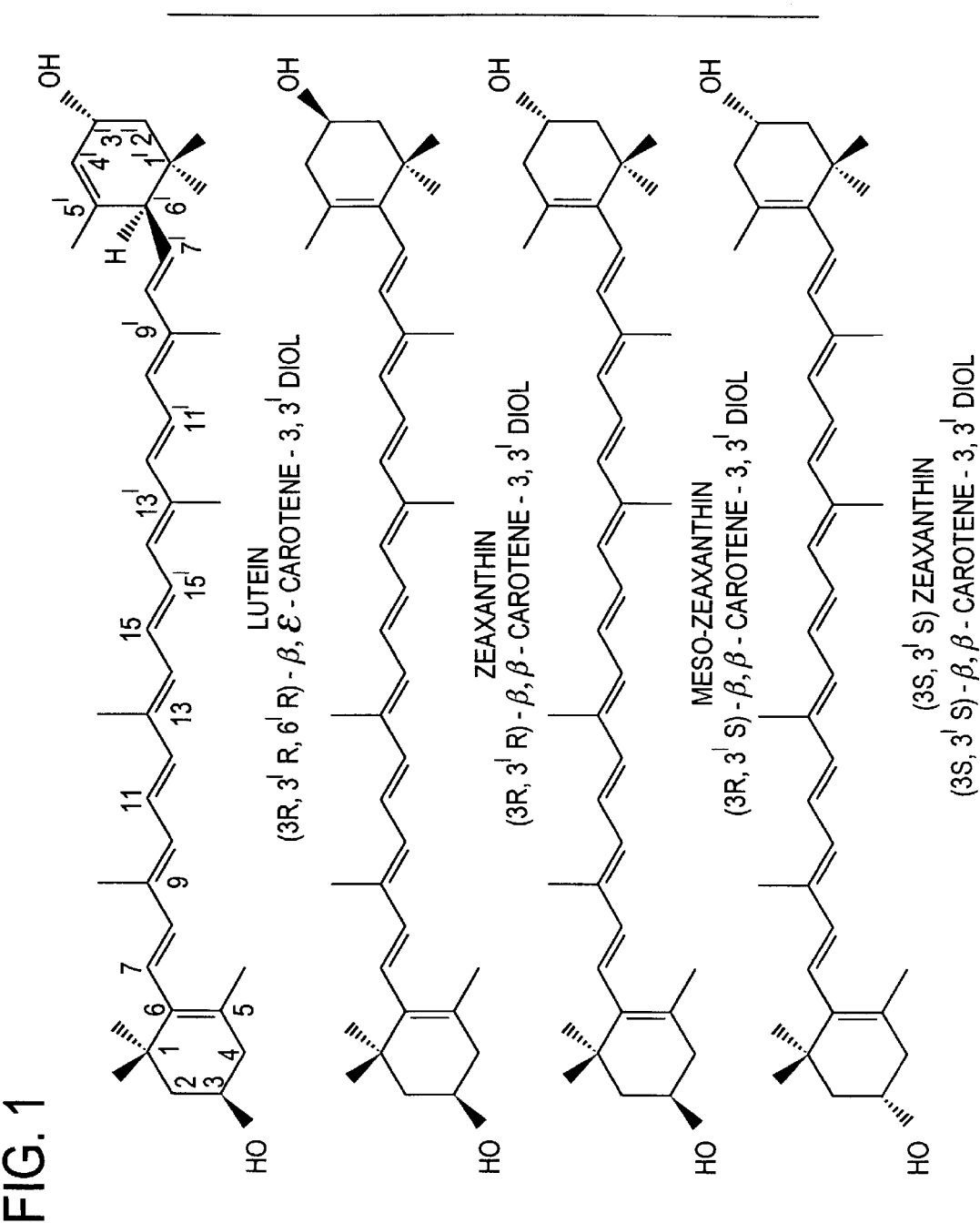
FIG. 1 shows compounds of the invention.
Figure 2:
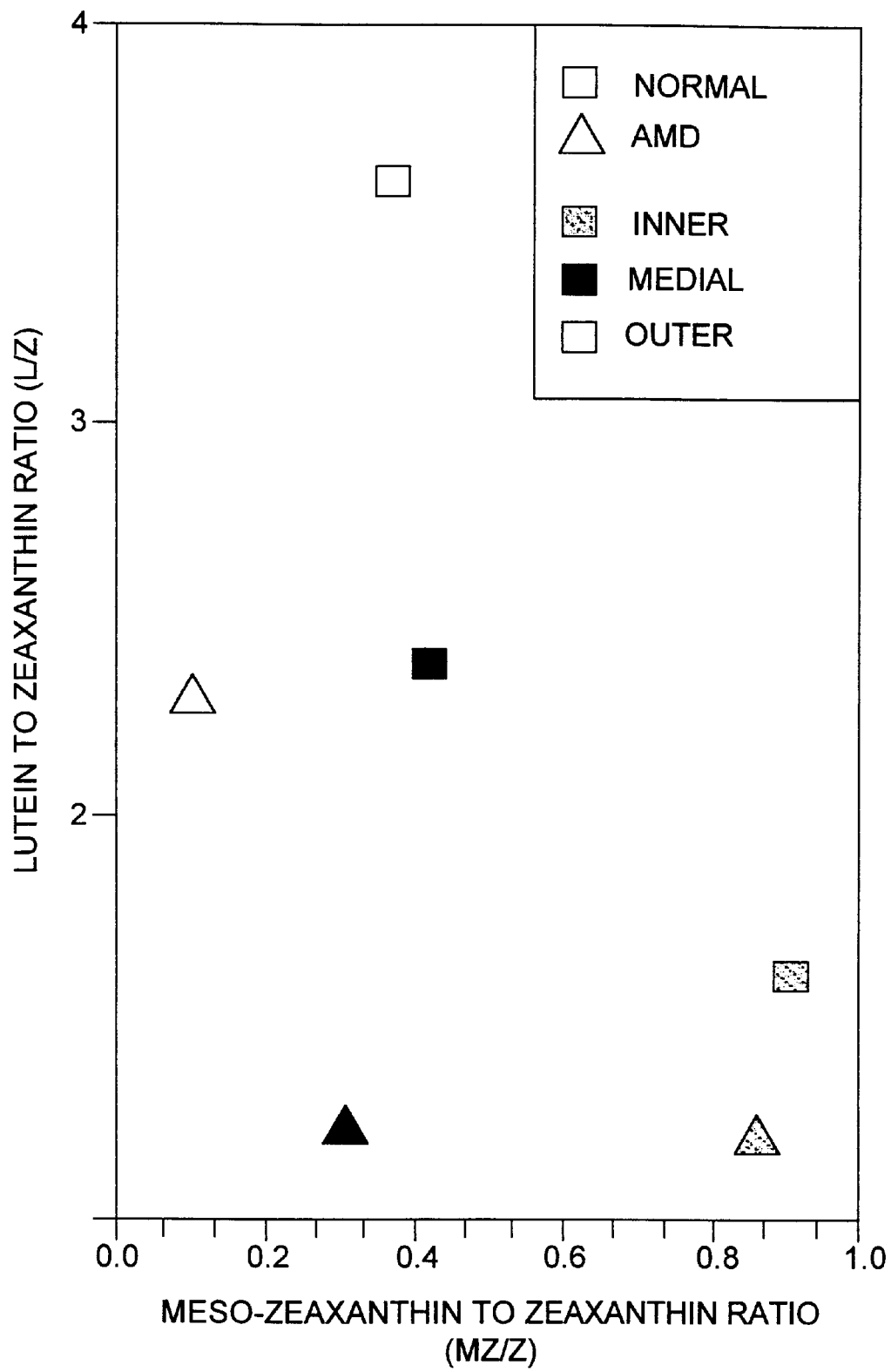
FIG. 2 shows for both normal and AMD eyes the average I:Z ratio for each disc or annulus of retinal tissue plotted against the average MZ:Z ratio. The ratios of lutein to zeaxanthin and meso-zeaxanthin are consistently lower for AMD eyes as compared to normals.

Carbamate derivatives of individual stereomers of both zeaxanthin and lutein were separated on a normal-phase HPLC column using the methods of Ruttiman et al (1983) and Schiedt et al (1995), the results being plotted in FIG. 2.

1.2 Results and Conclusions

As shown in the Table below, AMD eyes had on average approximately 70% of the total carotenoid found in controls, a figure that was very consistent across the retina. Seventeen (77%) of the twenty two AMD eyes had total amounts of lutein and zeaxanthin in the central 3 mm of the retina which were below the mean (5.9 pmole/mm$^2$) for the control group. For the two annuli, having outer diameters of 11 and 21 mm respectively, 15 (68%) of the AMD group were found to be lower in total carotenoids than the corresponding regions in the control group.

The differences observed between the control and AMD eyes in the inner annuli were found to be statistically significant (on a one sided test p<0.05); the difference in the medical and outer annuli were found almost significant (p<0.1).

The relative distributions of carotenoids throughout the retina for normal and AMD eyes were found to be essentially the same. Both groups were characterised by a decrease in the quantity of meso-zeaxanthin and a relative increase in lutein with increasing distance from the fovea. The relative amounts of lutein and meso-zeaxanthin as compared to zeaxanthin are consistently lower in the AMD retinas as compared to normal retinas.

| | TOTAL CAROTENOID/UNIT AREA (pmoles/mm$^2$) | | |
|---|---|---|---|
| Donor # | INNER (7.1 mm$^2$) | MEDIAL (93 mm$^2$) | OUTER (343 mm$^2$) |
| 1 | 12.8 | 0.88 | 0.19 |
| 2 | 10.5 | 0.51 | 0.10 |
| 3 | 10.4 | 0.89 | 0.18 |

-continued

TOTAL CAROTENOID/UNIT AREA (pmoles/mm$^2$)

| Donor # | INNER (7.1 mm$^2$) | MEDIAL (93 mm$^2$) | OUTER (343 mm$^2$) |
|---|---|---|---|
| 4 | 9.3 | 1.35 | 0.36 |
| 5 | 8.4 | 0.38 | 0.07 |
| 6 | 5.8 | 0.19 | 0.06 |
| 7 | 5.3 | 0.23 | 0.43 |
| CONTROL 8 | 5.1 | 0.48 | 0.21 |
| EYES 6 | 4.7 | 0.15 | 0.05 |
| 9 | 4.6 | 0.21 | 0.06 |
| 9 | 4.3 | 0.18 | 0.05 |
| 10 | 2.5 | 0.07 | 0.03 |
| 10 | 2.2 | 0.08 | 0.03 |
| 11 | 2.0 | 0.25 | 0.20 |
| 12 | 1.0 | 0.09 | 0.02 |
| Control average ± sd | 5.9 ± 3.4 | 0.04 ± 0.36 | 0.14 ± 0.12 |
| 13 | 9.5 | 0.47 | 0.19 |
| 13 | 9.4 | 0.78 | 0.23 |
| 14 | 8.4 | 0.30 | 0.12 |
| 14 | 7.7 | 0.56 | 0.13 |
| 15 | 6.7 | 0.17 | 0.09 |
| 16 | 5.7 | 0.24 | 0.08 |
| 17 | 4.8 | 0.47 | 0.15 |
| 18 | 4.5 | 0.34 | 0.07 |
| 16 | 4.5 | 0.20 | 0.06 |
| 19 | 4.5 | 0.14 | 0.05 |
| 17 | 4.0 | 0.24 | 0.11 |
| 19 | 3.8 | 0.05 | 0.09 |
| 20 | 3.4 | 0.45 | 0.16 |
| 21 | 3.4 | 0.20 | 0.09 |
| 20 | 2.4 | 0.46 | 0.13 |
| 22 | 2.3 | 0.13 | 0.05 |
| 22 | 1.9 | 0.11 | 0.06 |
| 23 | 1.2 | 0.03 | 0.02 |
| 1 | 0.71 | 0.47 | 0.19 |
| 23 | 0.46 | 0.03 | 0.02 |
| 24 | 0.43 | 0.10 | 0.03 |
| 24 | 0.32 | 0.07 | 0.02 |

EXAMPLE 2

Update of lutein in human adults 2.1 Serum Uptake

A trial was conducted to determine if dietary supplementation with lutein and zeaxanthin effectively can change the pigment levels in the macula.

The optical density of the macula pigment was measured for each subject using the method of flicker photometry (Bone and Sparrock 1971; Bone et al 1992). The concentration of pigment in the macula is proportioned to its optical density and the actual amount of pigment was assumed to be proportional to concentration. Thus, optical density was taken as a measure of the total amount of pigment.

Serum lutein and zeaxanthin was measured by conventional HPLC.

Two health adult males (of age/weight 42 year 60 kg and 51 years/61 kg) ingested the equivalent of 30 mg of lutein per day in the form of lutein esters (source; marigold flowers) suspended in 2 ml of canola oil. This was continued over a period of 138 days and then the dose of lutein was discontinued. Chemical analysis has shown that the product contains approximately 97% lutein and 3% zeaxanthin. Fasting serum lutein/zeaxanthin levels of both individuals were determined by conventional HPLC on the morning of the first dose as a measure of base line. Blood samples were drawn at 2–3 hour intervals throughout the first day for both subjects and then daily for the next three days. Following the first week of suplementation, blood samples were drawn weekly. Blood was collected into a standard Vacutainer serum separator tube containing no anitcoagulent. After allowing about 30 min for coagulation, the sample was centrifuged for 10 minutes and the serum removed by pipette. Serum samples were stored at −20° C. prior to analysis. Carotenoids were extracted from the serum by a minor modification of widely used methods (Guiliano et al, 1993; Handelmann et al, 1992). 200 μl aliquots of serum were diluted with 2 mL of 50% ethanol/water to ensure precipitation of protein components. 20 μl of an internal standard, monohexyl lutein ether, containing about 90 ng, was added to the solution at this point for quantification of the carotenoids by HPLC. This solution was extracted 3 times with 2 mL portions of hexane by vortexing the sample for 1 min followed by centrifuging for 5 minutes and pipetting off the hexane layer. The three portions of hexane were dried under a stream of nitrogen gas and stored under nitrogen at −20° C. until analysis was completed.

Serum extracts were dissolved in 40 μL of ethanol prior to injection. Samples were vigorously agitated on a vortex mixer for 1 min to ensure dissolution of the sample. Two replicate analyses were carried out using 20 μL aliquots. Serum carotenoids were eluted at a flow rate of 1 mL/min through a 15 cm×4.6 mm. Adsorbosphere ODS 3 μm HS column (Alltech) coupled to a 25 cm×4.6 m Spherisorb ODS 5 μm column (Keystone Scientific) with detection of the carotenoids of 461 nm.

Figure 3A:
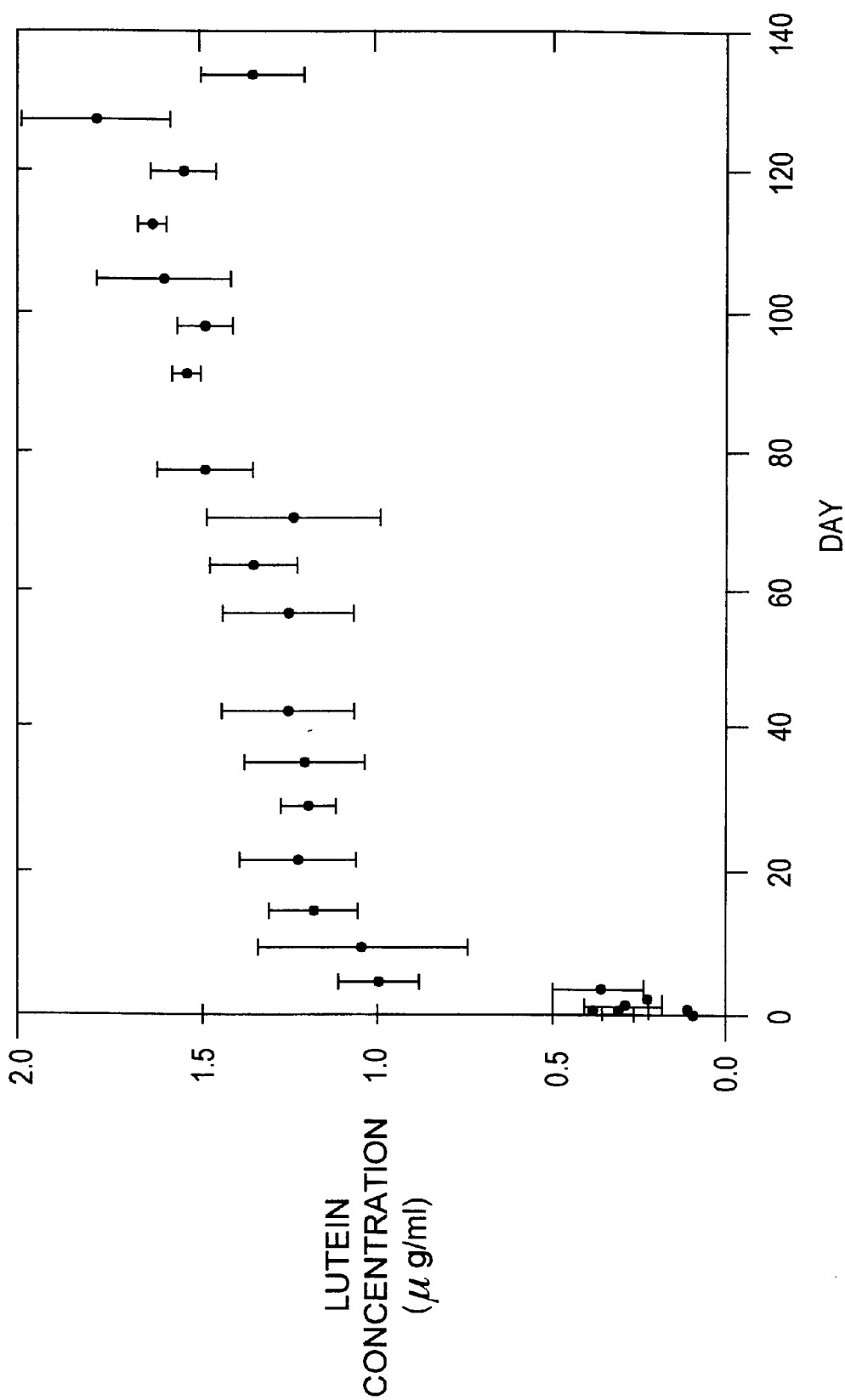
FIG. 3a shows the time dependent increase in the serum lutein level of Subject JTL (Example 2). Error bars represent the standard deviations in the measurements. Day "0" represents the beginning of lutein supplementation.
Figure 3B:
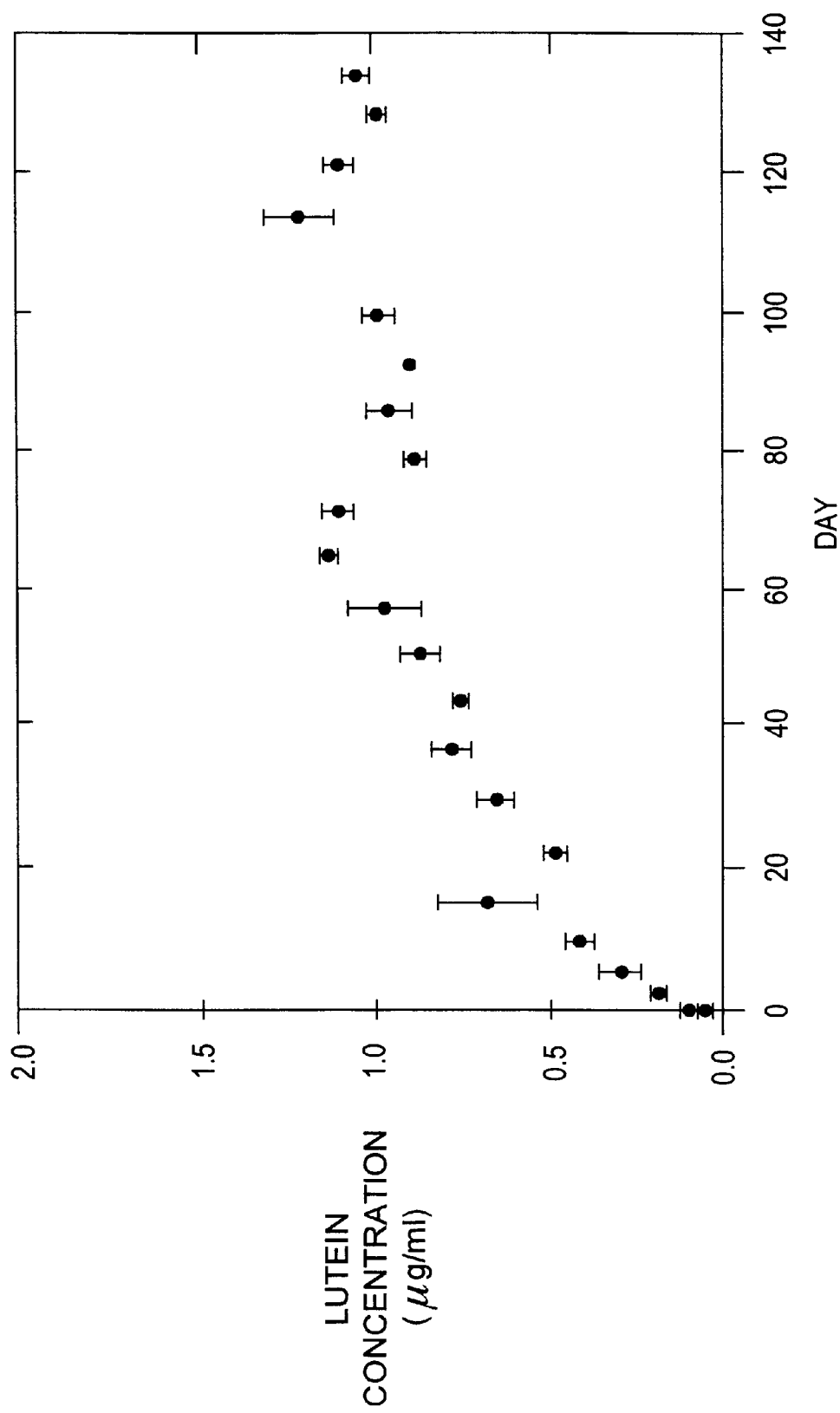
FIG. 3b shows the time dependent increase in the serum lutein level of subject RAB (Example 2). Error bars represent the standard deviations in the measurements. Day "0" represents the beginning of lutein supplmentation.

FIGS. 3a and 3b show the increase in serum lutein concentration in the two subjects during the time course of the supplementation experiment. The concentration of lutein in both subjects increased b a factor of about 10 times with the first week and remained high thereafter.

Two other subjects LLM and KES each receiving 30 mg/day lutein ester also showed large increases in serum lutein concentrations.

Subject LLM increased from 0.5 μg/m to 1.20 μg/ml in 50 days and then reached a plateau.

Subject KES increased from 0.20 μg/ml to 1.22 μg/ml in 50 days.

2.2 Macular Uptake

The optical density of the macular pigment was measured for each subject using the method of heterchomatic flicker photometry (Bone and Sparrock, 1971; Bone et al, 1992). The concentration of pigment in the macula is proportional to its optical density and the actual amount of pigment was assumed to be proportional to concentration. Thus optical density was taken to be a measure of the total mount of pigment.

In the flicker method, a small visual sitimulus is presented to the eye which alternates in wavelength between 460 nm, the peak abosorbance wavelength of the macular pigment, and 540 nm where pigment absorbance is zero (Bone et al, 1992). Above a certain frequency, color fusion occurs but the stimulus continues to flicker. At a higher frequency, a critical condition can be reached where flicker can be eliminated only if the two wavelength components are matched in luminance. If the stimulus is viewed peripherally, so that the image falls outside the macula, neither wavelength is attenuated by the macular pigment. However, if the stimulus is viewed centrally, the intensity of the 460 nm light must be increased to compensate for absorption by the macular pigment in order to achieve a luminance match. Thus it is possible to determine the optical density of a subject's macular pigment at the peak wavelength, or indeed any other wavelength.

The validity of this technique depends on the relative spectral response of the receptors being the same in the central and peripheral locations used. The flicker, which the subject seeks to eliminate, is one of luminance and, assuming phototopic conditions, luminance is most likely due to an additive response from the long and middle wavelength sensitive cones (Guth et al, 1980). There is evidence that these two cone types are present in equal ratios in the two locations used (Wooten and Wald, 1973). The short wavelength cones, whose relative abundances differ between the two locations, are generally not assumed to contribute to luminance (Guth et al, 1980), though others, using flicker techniques, have sought to eliminate their participation (Pease et al, 1987; Werner et al, 1987; Hammond et al 1995a). The ultimate justification for our procedure is to be found in the accurate reproduction of the macular pigment absorbance spectrum which it generates (Bone et al, 1992).

The apparatus consisted of a two-channel Maxwellian view system based on a single light source, a 75 W xenon arc lamp. The wavelengths of the two channels were determined by 460 nm and 540 nm interference filters respectively, having half-widths of 7 and 9 nm. The channels were combined by a rotating semicircular mirror, and a circular aperture in a white screen provided a 1.5° diameter stimulus. Cross-hairs facilitated central fixation of the stimulus. The screen was 18° in diameter and was illuminated with white light from the same source. The illuminance of the screen was adjusted to provide the same retinal illuminance of 4 log Td as the stimulus. This was considered to be sufficiently high to minimize problems associated with rod intrusion which could otherwise differentially affect measurements in the macula and peripheral retina (Wyszcki and Stiles, 1982). A small red LED was located 8° above the centre of the stimulus to provide a fixation mark for peripheral viewing of the stimulus. The intensity of the 460 nm channel was adjustable by the subject through a neutral density, compensated wedge whose setting could be recorded by a push-button. The flicker frequency was also under the subject's control via a potentiometer. An adjustable dental impression bite ensured accurate and steady positioning of the subject's eye relative to the exit pupil.

The flicker frequency was set to a predetermined value which, for central viewing by the subject, would allow flicker to be eliminated only over a very small range of wedge settings. This frequency was in the 25 to 35 Hz range. Having set the wedge to meet the no-flicker condition, the subject adapted to the viewing conditions by fixating with one eye on the stimulus cross-hairs for two minutes. The subject's other eye was occluded by an eye-patch. At the end of this period, the subject proceeded to make a series of 10 to 15 wedge settings, attempting to obtain the center of the no-flicker range. The wedge was randomly offset after each setting. On occasions, the subject could not eliminate flicker entirely but instead sought a condition of minimum flicker. This was followed by another series of 10 to 15 settings while fixating on the LED, the frequency having been reduced to 12 to 16 Hz in order to reduce the range of no-flicker. The whole procedure was then repeated for the subject's other eye. The optical density of the macular pigment of the subject was measured daily for a period of one week prior to the commencement of lutein supplementation, and daily thereafter.

Figure 4A:
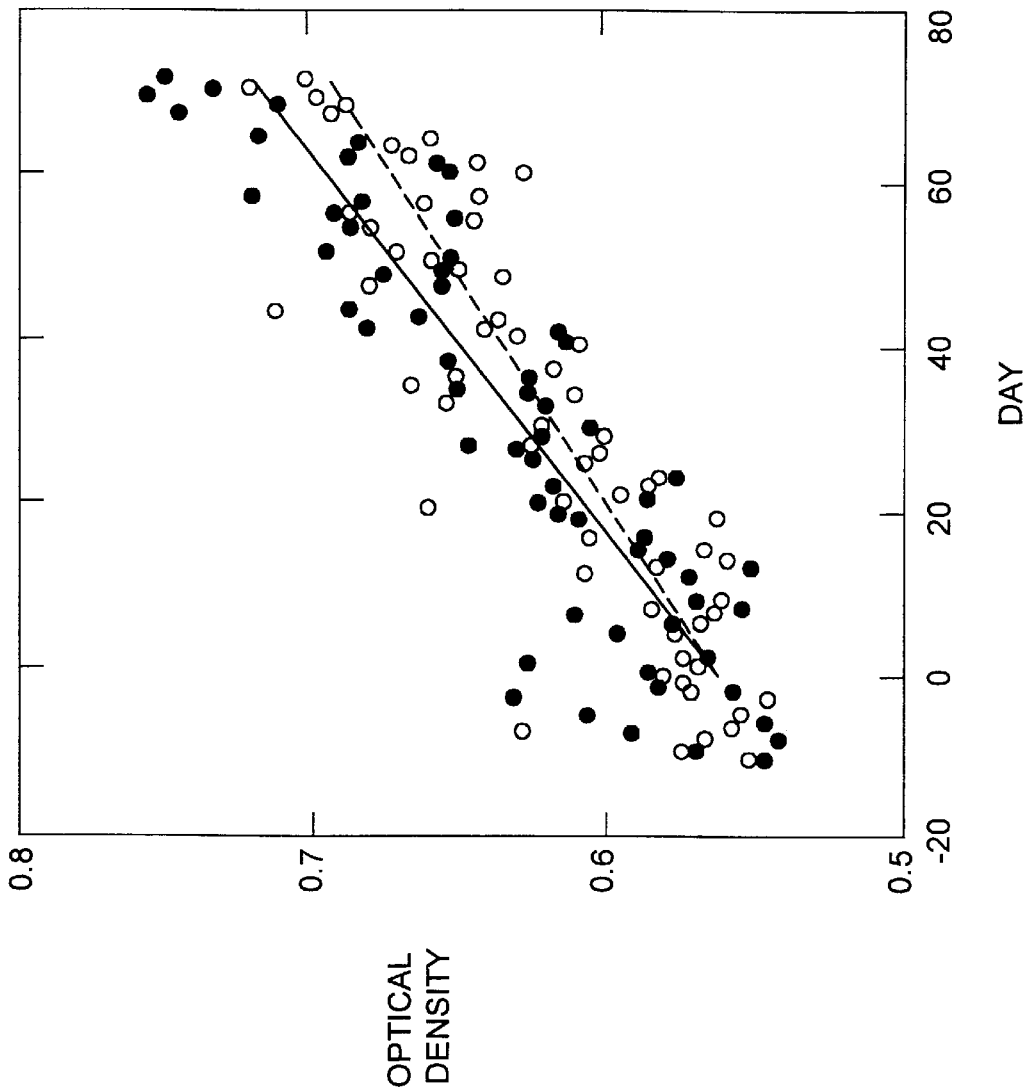
FIG. 4a shows the daily macular pigment optical density measurements for subject JTL (Example 2) from 7 days prior to the start (day "0") of the lutein supplementation through day 72. Left eye—solid circles; right eye—open circles. The solid line is the linear least squares fit to the left eye data and has a slope of $15.3 \times 10^{-3}$ absorbance units per week. The dashed line is a fit to the right eye data and has a slope of $12.5 \times 10^{-8}$ absorbance units per week.
Figure 4B:
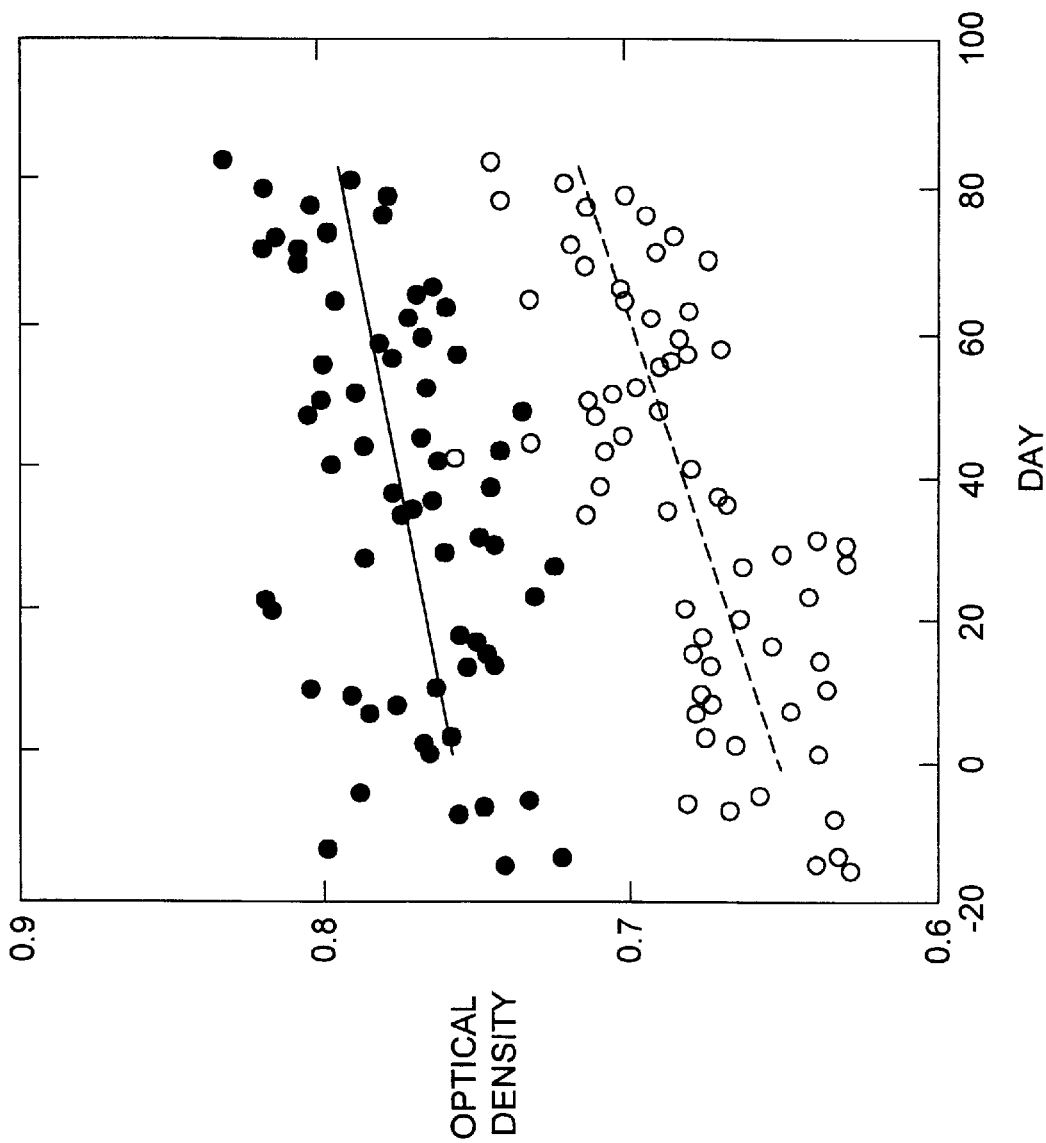
FIG. 4b shows the daily macular pigment optical density measurements for subject RAB (Example 2) from 7 days prior to the start (day "0") of the lutein supplementation through day 83. Left eye—solid circles; right eye—open circles. The solid line is the linear least squares fit to the left eye data and has a slope of $3.1 \times 10^{-3}$ absorbance units per week. The dashed line is a fit to the right eye data and has a slope of $2.3 \times 10^{-3}$ absorbance units per week.
Figure 5A:
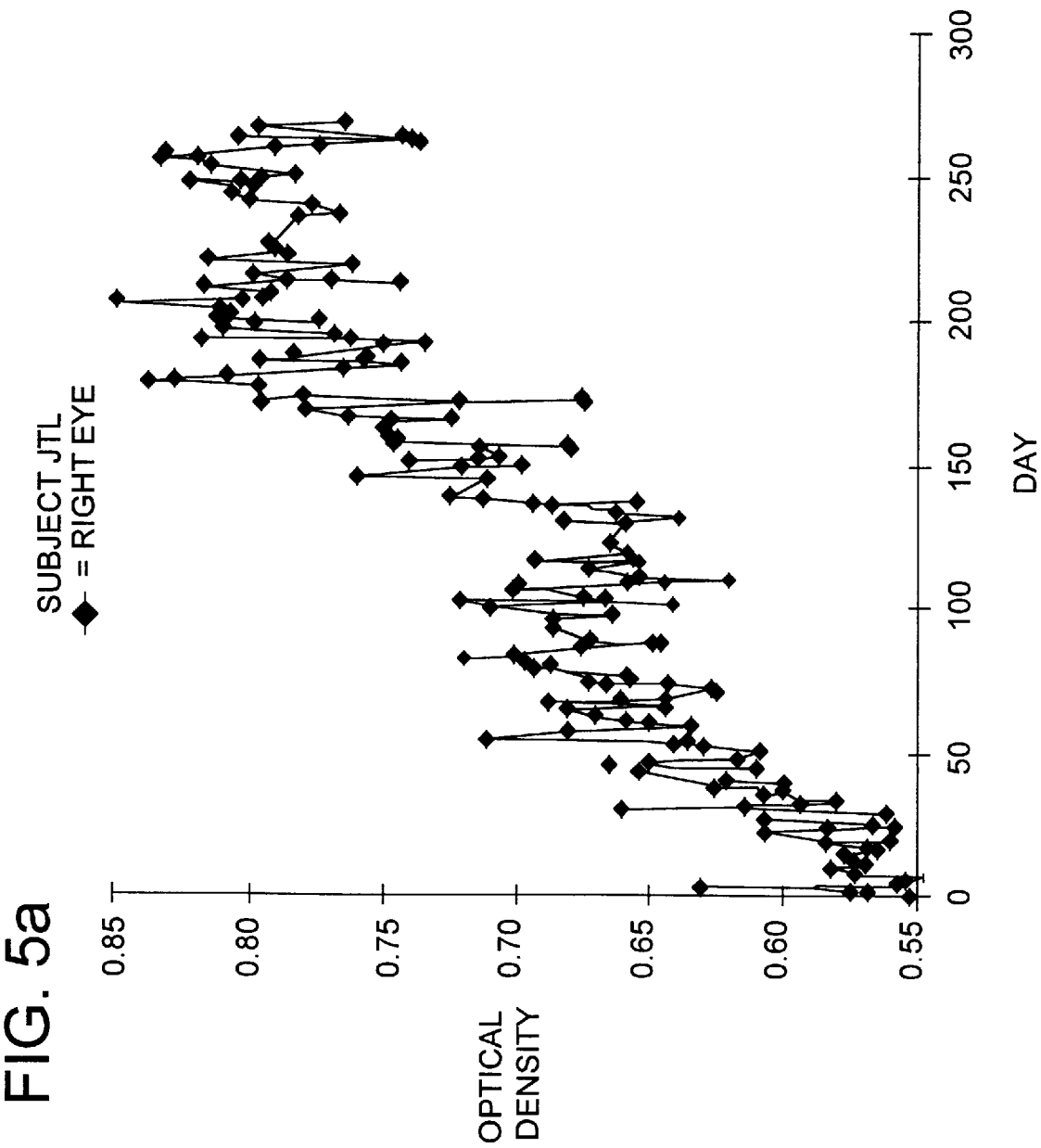
FIGS. 5a, 5b and 5c show the daily macular pigment optical density measurements for the same subject as is the case in FIG. 4a for a longer period of lutein administration which includes the period represented in FIG. 4a, FIG. 5arelating to the right eye of the subject, FIG. 5b relating to the left and FIG. 5c representing the L-R average.
Figure 5B:
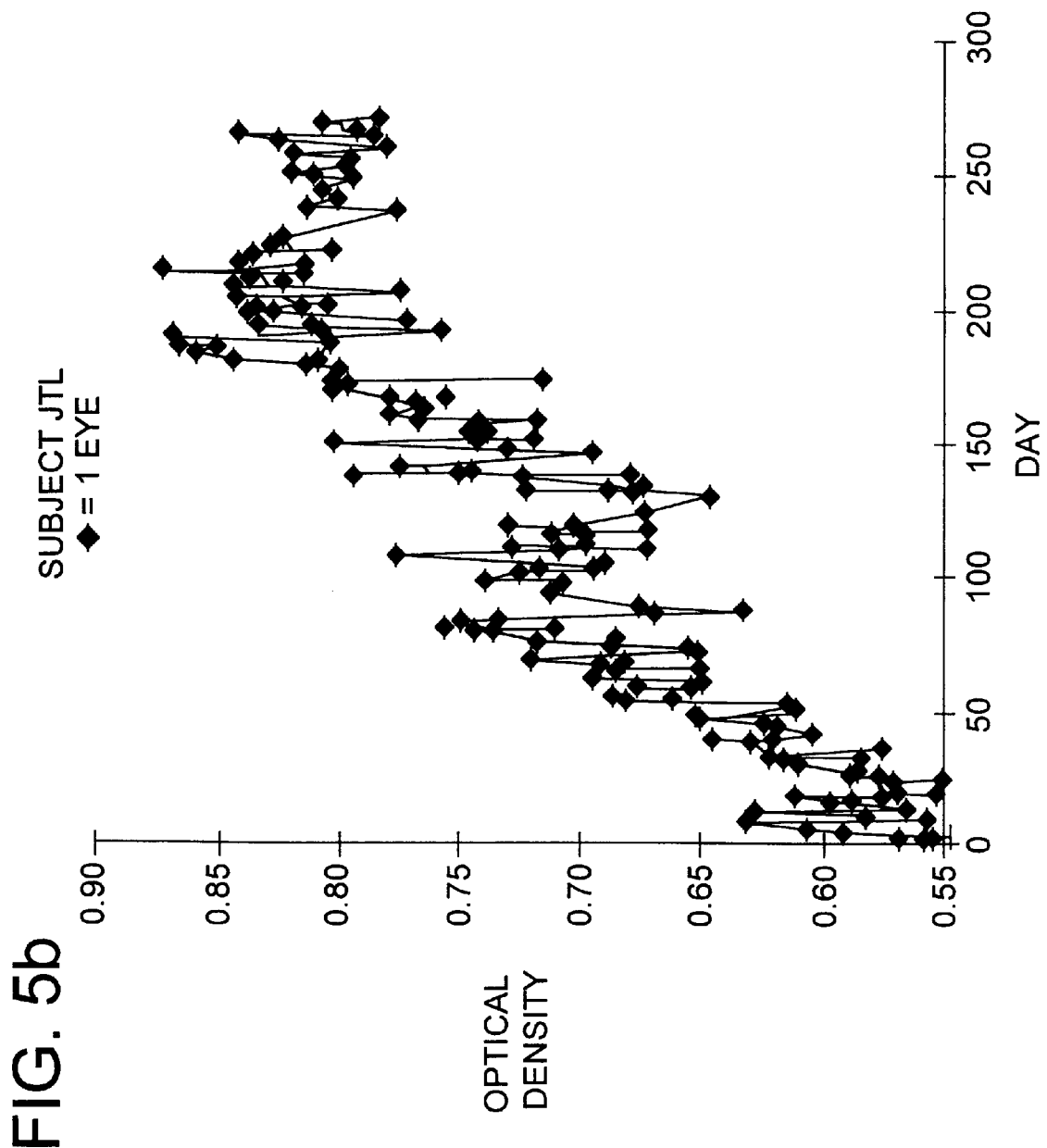
Figure 5C:
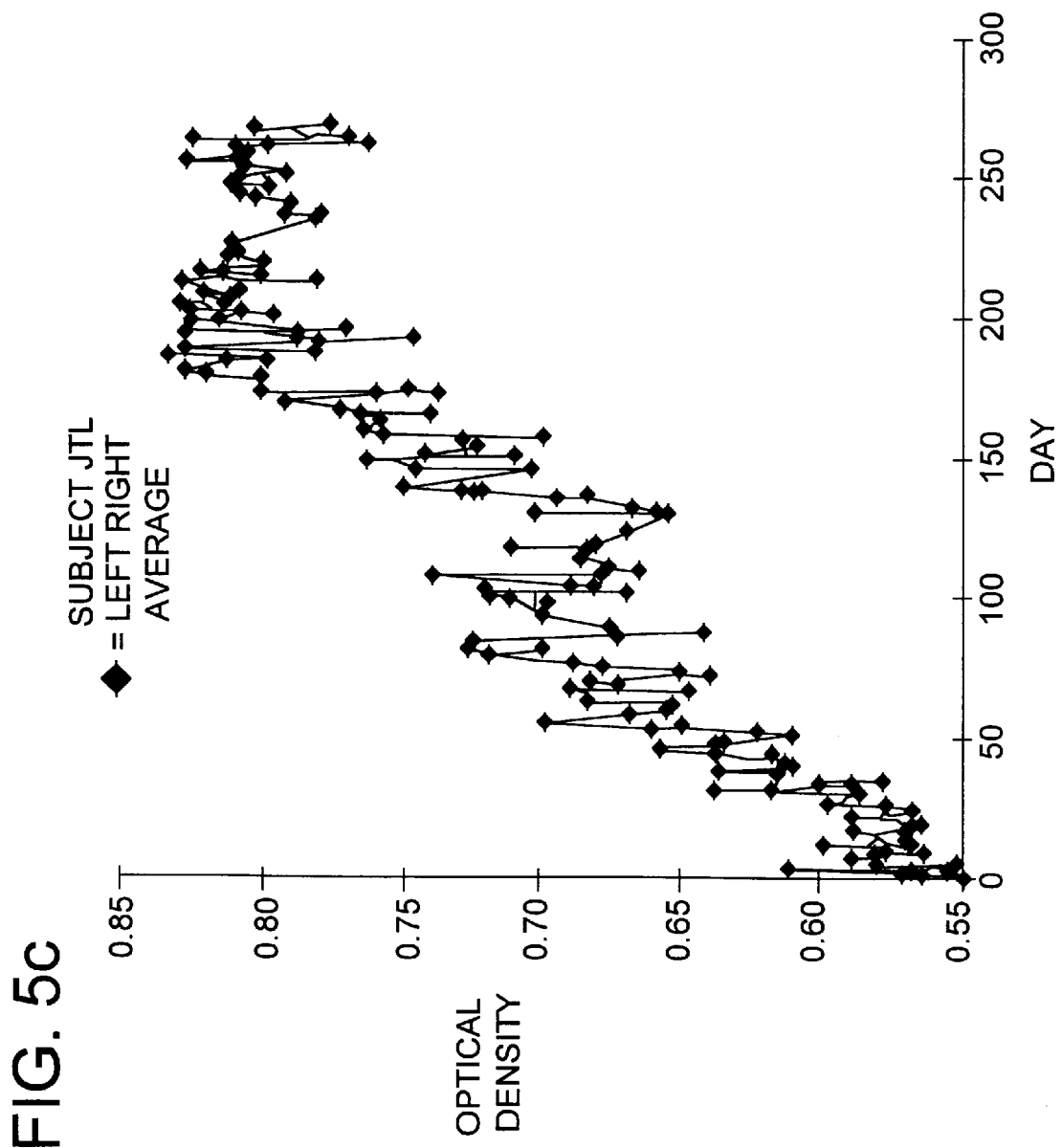
Figure 6:
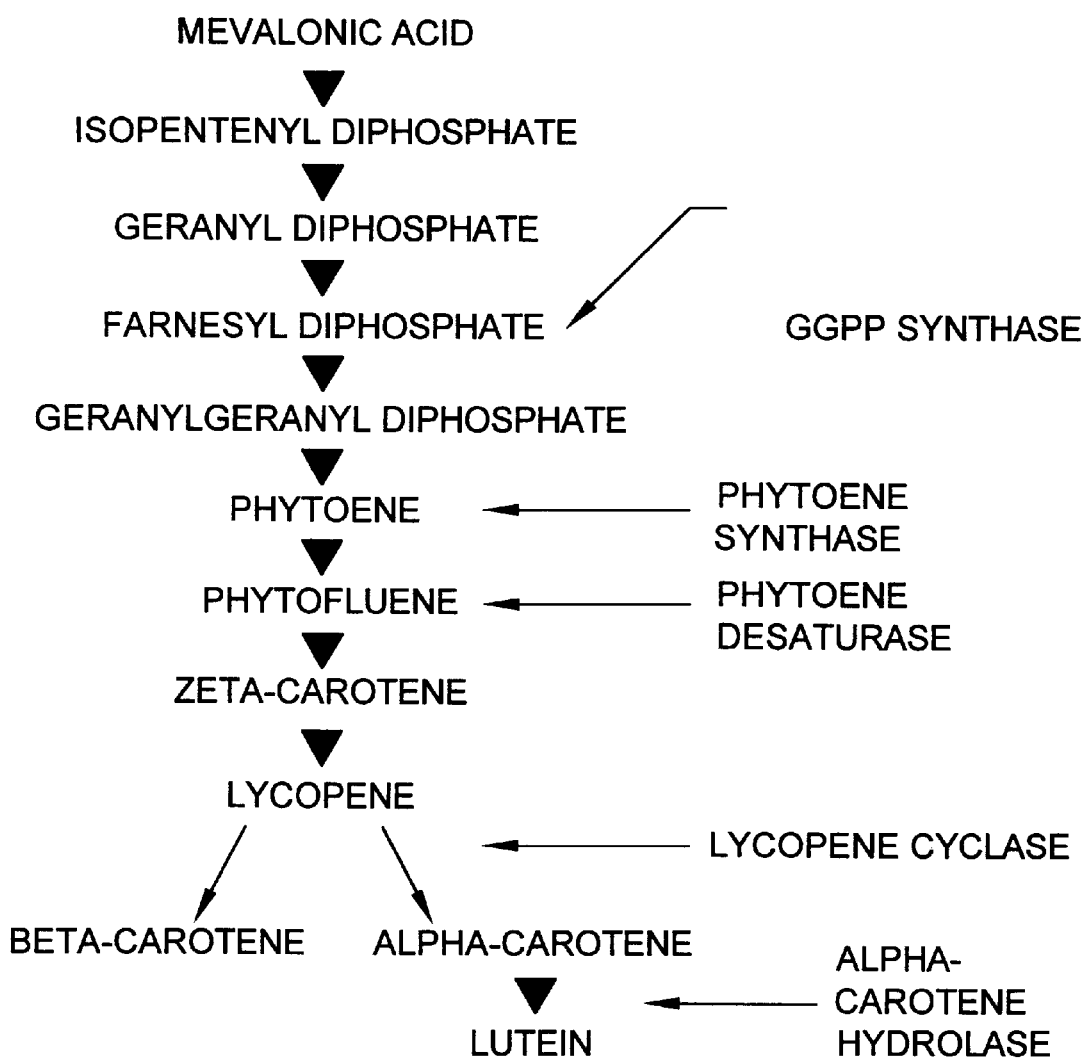
FIG. 6 depicts the carotenoid biosynthesis pathway in lutein-producing plants.

FIGS. 4a and 4b show the absorbency of the macular pigment during the time course of the experiments in the two subjects. An increase in the macular pigment level of subject JTL was first observable on the 14th day of supplementation. This subject had macular pigment levels in both eyes that were experimentally determined by repeated measurements to be equal (±2%) the initial values of 0.57 and 0.58 being determined by averaging 15 measurements obtained over a 17 day time period. Comparison of these values with the average of 15 measurements obtained over the 18 day period at the end of the experiment gave values of 0.67 and 0.70 for the right and left eye, respectively, showing that the increase in optical density of the macular pigment is highly significant $p<0.0005$ for both the right and left eye, based on a one sided t test. After discontinuing the dose of lutein at day 138, optical density continued to rise until about day 180 and then reached a plateau.

For subject RAB, right and left eyes were found to have significantly different macular pigment density. The initial mean value for the right eye was 0.66 while that of the left eye was 0.76. This corresponded to a difference of 15% between the subject's left and right eyes. The increase in macular pigment determined by comparing the initial averages for each eye and the final average (0.70 right, 0.79 left) was found to be highly significant ($p<0.001$).

After discontinuing the dose at day 138, the optical density continued to rise in both eyes until day 200 and then reached a plateau. After several weeks of administration of lutein, the palms of the hands of each subject turned a noticeable yellow colour. This condition is similar to that induced by beta-carotene at the same dose.

Two other subjects LLM and KES receiving 30 mg/day lutein ester were examined.

For subject LLM after 75 days the macular pigment had increased in both eyes from 0.3 to 0.5 optical density and then reached a plateau.

For subject KES, the data had a much larger spread of values and an increase was only apparent in the left eye of optical density from 0.3 to 0.5.

Macular pigmentation increase was shown to be a slow process, despite the high plasma lutein levels. This may be partly due to the need for lutein to diffuse into the avascular macular region of the retina.

The trial established a relationship between the increased serum levels of lutein and corresponding increases in the concentration of lutein in the macula of the human eye. Long term lutein supplement of individuals having low levels of macular pigmentation could result in a significant increase in the level of pigmentation within the macula.

Our data suggests that macular pigmentation does function to protect the retina. An increased rate of photo oxidation might accompany lower macular pigment levels in some individuals and could contribute to a more rapid build up of pathological lesions associated with AMD.

Example 3

A capsule was prepared using the following ingredients by simple admixture and routine encapsulations:

| Ingredients per capsule | Label Claim | mg per Capsule |
| --- | --- | --- |
| Lutein Ester | 30 mg Lutein | 200 |
| Lecithin | | 50 |
| Soya Bean oil | | 200 |

One capsule per day/after a meal is recommended

In the above example, lutein ester can be replaced by a mixture of isomers of zeaxanthin (normal zeaxanthin, meso zeaxanthin and 3S3'S zeaxanthin).

Example 4

A capsule was prepared using the following ingredients by simple admixture and routine encapsulation:

| Ingredients per capsule | Label Claim | mg per Capsule |
| --- | --- | --- |
| Lutein Ester | 10 mg Lutein | 75 |
| Zeaxanthin Ester | 10 mg zeaxanthin | 75 |
| Lecithin | | 25 |
| Soya Bean Oil | | 100 |

The above is a mixture of 50% each carotenoid. In the above capsule, zeaxanthin could represent all its isomers (zeaxanthin, meso zeaxanthin and 3S 3's zeaxanthin).

Example 5

A capsule was prepared using the following ingredients by simple admixture and routine encapsulation:

| Ingredients per capsule | Label Claim | mg per Capsule |
| --- | --- | --- |
| Vitamin C (ascorbic Acid) | 150 mg | 160 |
| a-tocopheral | 100 mg | 110 |
| Lutein Ester | 15 mg Lutein | 90 |
| Lecithin | | 25 |
| Soya Bean Oil | | 75 |

A suitable daily dose for treatment AMD would be two capsules daily.

Example 6

The procedure of Example 7 was repeated except that 30 mg of Coenzyme Q10 was included in the mixture.

Example 7

A size 12 oval capsule of nominally 800 mg weight was prepared from the following ingredients by simple admixture and routine encapsulation:

| Ingredients per capsule | Label Claim | mg per Capsule |
| --- | --- | --- |
| Vitamin A Palmitate 1500 lu/gm | 500 RE | 1.277 |
| Carotene Oil | 15 mg BC | 52.5 |
| Lutein Ester* | 7.5 mg Lutein | 50 |
| Vitamin C (Ascorbic Acid) | 100 mg | 105 |
| Mixed Tocopherols 1000 iu/gm | 100 mg | 149 |
| Selenium Yeast 1000 mcg/gm | 90 mcg | 90 |
| Copper Gluconate to give | 3 mg Cu | 22.26 |
| Zinc Gluconate to give | 15 mg Zn | 117 |
| Manganese Gluconate to give | 4 mg Mn | 36.4 |
| Vegetable Shortening | | 56 |
| Beeswax | | 23 |
| Lecithin | | 22 |
| Soya Bean Oil | | 75.563 |
| | | 800 |

*concentrated lutein esters with an E (1%, 1 cm) of 300 to 340 at 453 nm in chloroform-corresponds to a pure lutein content of 12 to 14.4%.

One capsule per day is very suitable for long term administration and has in addition valuable antioxidant properties.

Example 8

A dry powder formula diet composition was prepared by mixing 150 mg of lutein ester per day with a Cambridge Diet (The Cambridge Diet is a Registered Trade Mark) product obtained from Cambridge Health Plan Ltd, Norwich, England under the product identification.

Example 9

Tomato plants were genetically engineered to contain circa 15 mg lutein per 100 g using the method described in PCT Application No WO92/16635.

A consumption of 100–200 g per day is a useful quantity of tomatoes to provide lutein for incorporation into the macula.

References

Bone, R. A. and Landrum, J. T. (1984). Macular pigment in Henle fiber membranes: a model for Haidinger,s brushes. *Vision Res* 24, 103–108.

Bone, R. A. and Landrum, J. T., and Cains, A. (1982). Optical density of the macular pigment in vivo and in vitro. *Vision Res.* 32, 105–110.

Bone, R. A. and Landrum, J. T., Hime, G. W., Cains, A. and Zamor, J. (1993). Stereochemistry of the human macular carotenoids. *Invest. Ophthalmol. Vis. Sci.* 34, 2033–2040.

Bone, R. A. and Landrum, J. T., and Tarsis, S. I., (1985). Preliminary identification of the human macular pigment. *Vision Res.* 25, 1531–1535.

Bone, R. A. and Sparrock, J. M. B. (1971). Comparison of macular pigment densities in human eyes. *Vision Res.* 11, 1057–1064.

Davson, H. (1990), "Physiology of the Eye", Pergamon Press, Inc., New York.

Ditchbum, R. W. (1973). "Eye-Movements and Visual Perception", Clarendon Press, Oxford.

Eye Disease Case—Control Study Group (1993). Antioxidant status and neovascular age-related macular degeneration. Arch. Ophthalmol. 111, 104–109.

Feeney-Burns, L., and Ellersieck, M. R. (1985), Age-related changes in the ultrastructure of Bruch,s membrane. *Am. I. Ophthalmol.* 100, 686–697.

Gottsch, J. D., Pou, S., Bynoa, L. A., and Rosen, G. M. (1990). Hematogenous photosensitization. A mechanism for development of age-related macular degeneration. *Invest. Ophthalmol. Vis. Sci.* 31, 1674–1692.

Guiliano, A. R., Matzner, M. B., and Canfield, L. M. (1993). Assessing variability in quantitation of carotenoids in human plasma: variance component model. In "Methods in Enzymology" (L. Packer, ed.), Vol 214, pp. 94–101. Academic Press, San Diego.

Guth, S. L., Massof, R. W., and Benzschawel, T. (1980). Vector model for normal and dichromatic colour vision. *I. Opt. Soc. Am.* 70, 197–212. Hammond, B. R., Jr., Fuld, K., and Curran-Celentano, J. (1995a). Macular pigment density in monozygotic twins. *Invest. Ophthalmol. Vis. Sci.* 36, 2531–3541.

Handelmann, G. J., Shen, B., and Krinsky, N. I. (1992). High resolution analysis of carotenoids in human plasma by high-performance liquid chromatography. In "Methods in Enzymology" (L. Packer, ed.), Vol 213, pp. 336–346. Academic Press, San Diego.

Kirshfeld, K. (1982). Carotenoid pigments: their possible role in protecting against photooxidation in eyes and photoreceptor cells. *Proc. R. Soc. Lond.* B216, 71–85.

Landrum, J. T., Bone, R. A., Vidal, I., Menendez, E. and Kilburn, M. (1995). Macular pigment stereomers in individual eyes: a comparison between normals and those with age-related macular degeneration. Arch. Ophthalmol. 113, 1518–1523.

Mares-Perlman, J. A., Brady, W. E., Klein, R., Klein, B. E. K., Palta, M., Bowen, P., and Stacewicz-Sapuntzakis, M. (1994). Serum levels of carotenoids and tocopherols in people with age-related maculopathy. Invest. Ophthalmol. Vis. Sci. 95, (supply) 3455.

Pease, P. L., Adam, A. J., and Nuccio, E. (1987). Optical density of human macular pigment. Vision Res. 27, 705–710.

Reading, V. M., and Weale, R. A. (1974). Macular pigment and chromatic aberration. I. Opt Soc. Am. 64, 231–234.

Ruttlmann, A., Schiedt, T., and Vecci, M. (1983). Separation of (3R,3'R)-, (3R,3'S; meso)- (3S,3'S)-zeaxanthin, (3R,3'R,6'R)-(3R,3'S,6'S)-, and (3S,3'S,6'S)-lutein via the dicarbamates of (S)-(−)-1-[1-naphthyl]]ethylisocyanate. I. High. Res. Chrom. Commun. 6, 612–616.

Scheidt, K., Bischof, S., and Glinz, E. (1995). Example 5: Fish-isolation of astaxanthin and its metabolites from skin of Atlantic Salmon (Salmo salor). In "Carotenoids" (G. Britton, S. Liaaen-Jenson, H. Pfander, eds.), pp. 243–252. Birkhauser Verlag, Basel.

Seddan, J. M., Umed, A. et al. (1994). Dietary Cerotenoids, Vitamins A, C, and E, and Advanced Age-Related Macular Degeneration. J. A. M. A., 272, 1413–1420.

Weld, G. (1945). "Human vision and the spectrum". Nature (London), 101, 653–658.

Walls, G. L. (1967). "The vertebrate Eye and its Adaptive Radiation". Hafner, New York.

Werner, J. S., Donnelly, S. K., and Kliegl, R. (1987). Ageing and human macular pigment density. Appended with translations from the work of Max Schutze and Ewald Hering. Vision Res. 27, 257–268.

Wooten, B. R., and Wald, G. (1973). Colorvision mechanism in the peripheral retinas of normal and dichrometic observers. I. Gen. Physiol. 61, 125–145.

Wysecki, G., and Stiles, W. S. (1982). "Quantitative Deta and Formulae", Wiley, New York.

What is claimed is:

1. A method of therapy or prevention of age-related macular degeneration in a human subject by increasing deposition of yellow macular pigment in the macula of an eye of the subject, the method comprising orally administering to the subject a sufficient amount of mesozeaxanthin to increase the serum concentration of carotenoid(s) in the subject to at least 0.5 µg/ml and maintain the increased serum carotenoid concentration at or above 0.5 µg/ml for at least 14 days, and at least until the macular concentration of carotenoid(s) has achieved equilibrium.

2. A method as claimed in claim 1 wherein the daily dose of mesozeaxanthin is from 10 to 50 mg per day.

3. A method as claimed in claim 1 wherein the daily dose of mesozeaxanthin is at least about 30 mg per day.

4. A method as claimed in claim 1 wherein the daily dose of mesozeaxanthin is from 0.167 to 0.833 mg/kg body weight.

5. A method as claimed in claim 4 wherein said daily dose of mesozeaxanthin is about 0.5 mg/kg body weight.

6. A method as claimed in claim 1 wherein mesozeaxanthin is administered in ester form.

7. A method as claimed in claim 1 wherein mesozeaxanthin is administered in the form of a pharmaceutical composition.

8. A method as claimed in claim 7 wherein the pharmaceutical composition is a mixture comprising mesozeaxanthin in ester form together with lecithin and soya bean oil.

9. A method as claimed in claim 8 wherein the pharmaceutical composition additionally comprises lutein or zeaxanthin.

10. A method as claimed in claim 7 wherein the pharmaceutical composition contains at least one other biologically-active constituent.

11. A method as claimed in claim 10 wherein the other biologically-active constituent is an anti-oxidant.

12. A method as claimed in claim 11 wherein said anti-oxidant is an anti-oxidant selected from the group consisting of vitamin A, vitamin C, vitamin E, selenium, copper, zinc, manganese, ubiquinone (Co enzyme Q10) and mixtures thereof.

13. A method as claimed in claim 11 wherein said anti-oxidant is a carotenoid other than a zeaxanthin and other than lutein.

14. A method as claimed in claim 13 wherein the other carotenoid in the pharmaceutical composition is selected from the group consisting of lycopene, alpha, beta, gamma, and delta carotene and mixtures thereof.

15. A method as claimed in claim 7 wherein the pharmaceutical composition includes a pharmaceutically-acceptable carrier.

16. A method as claimed in claim 7 wherein the pharmaceutical composition is in unit dosage form.

17. A method as claimed in claim 16 wherein the pharmaceutical composition is in a form selected from the group consisting of tablets, capsules, powders and suspensions.

18. A method as claimed in claim 1 wherein the mesozeaxanthin administration is effected in a first treatment regime comprises of administration of the mesozeaxanthin for at least 14 days and until the subject serum levels thereof reach an equilibrium concentration 0.5 µg/ml or more and thereafter in a second treatment regime comprises of administration of a maintenance dose of mesozeaxanthin of 10 mg per day or more but less than 30 mg per day.

19. A pharmaceutical treatment course package comprising means defining accessibly closed individual receptacles retaining respective dosage units of a pharmaceutical composition comprising an active mesozeaxanthin component together with a carrier, said receptacles being arranged in the package in a first group of high dosage units and a second group of lower dosage units, the first group of receptacles numbering at least 14 and having in each at least one dosage unit providing a total dosage of at least 10 mg/receptacle of mesozeaxanthin.

20. A package as claimed in claim 19 wherein the second group of receptacles number at least 14.

21. A package as claimed in claim 20 wherein the second group of receptacles have in each at least one dosage unit providing a total dosage of not more than 7.5 mg/receptacle of mesozeaxanthin.

22. A package as claimed in claim 19 wherein each dosage unit in the first group of receptacles provides a dose of at least about 30 mg of mesozeaxanthin.

23. A package as claimed in claim 19 wherein said pharmaceutical composition includes a further carotenoid selected from the group consisting of lycopene, alpha, beta, gamma and delta carotene and mixtures thereof.

* * * * *